(12) United States Patent
Bhowmick et al.

(10) Patent No.: US 8,499,758 B2
(45) Date of Patent: Aug. 6, 2013

(54) INHALATION DEVICE

(75) Inventors: Subhas Balaram Bhowmick, Baroda (IN); Prashant Kane, Baroda (IN); Ganesh Sangaiah, Baroda (IN); Satish Madhukar Gokhale, Pune (IN); Ajay Nandgaonkar, Pune (IN); Abhijit Takale, Pune (IN); Simon James Smith, Hertford (GB); Samantha Anne Musgrave, Cambridge (GB); Richard Francis Day, Great Cambourne (GB); Lee Wood, Bridgend (GB); Becky Lynn Pilditch, St. Neots (GB); David Stuart Harris, Cambridge (GB); Jonathan Hugh Wilkins, Cambridge (GB); Duncan Aleck Bishop, Alconbury (GB); Matthew David Allen, Cambridge (GB)

(73) Assignee: Sun Pharma Advanced Research Company Ltd., Mumbai (IN)

( * ) Notice: Subject to any disclaimer, the term of this patent is extended or adjusted under 35 U.S.C. 154(b) by 776 days.

(21) Appl. No.: 12/598,241

(22) PCT Filed: Apr. 30, 2008

(86) PCT No.: PCT/IN2008/000277
§ 371 (c)(1),
(2), (4) Date: Feb. 23, 2010

(87) PCT Pub. No.: WO2009/008001
PCT Pub. Date: Jan. 15, 2009

(65) Prior Publication Data
US 2010/0163042 A1    Jul. 1, 2010

(30) Foreign Application Priority Data

Apr. 30, 2007    (IN) .......................... 841/MUM/2007

(51) Int. Cl.
*A61M 15/00*    (2006.01)
*A61M 16/00*    (2006.01)
(52) U.S. Cl.
USPC ............. 128/203.15; 128/203.21; 128/203.12
(58) Field of Classification Search
USPC ............. 128/203.12, 203.15, 203.18, 203.21
See application file for complete search history.

(56) References Cited

U.S. PATENT DOCUMENTS

| 6,550,477 | B1 | 4/2003 | Casper et al. | |
|---|---|---|---|---|
| 2002/0033176 | A1 | 3/2002 | Casper et al. | |
| 2003/0131781 | A1* | 7/2003 | Halstead et al. | 116/308 |

(Continued)

FOREIGN PATENT DOCUMENTS

| WO | 92/08509 A1 | 5/1992 |
|---|---|---|
| WO | 2006/079746 A1 | 8/2006 |
| WO | 2006/079747 A1 | 8/2006 |

OTHER PUBLICATIONS

International Search Report of PCT/IN2008/000277, mailing date of Feb. 25, 2009.

*Primary Examiner* — Theodore J Stigell
*Assistant Examiner* — Leah Stohr
(74) *Attorney, Agent, or Firm* — Sughrue Mion, PLLC

(57) ABSTRACT

The present invention relates to an inhalation-activatable device for administration of medicament in powder form to the respiratory system of a patient.

20 Claims, 11 Drawing Sheets

U.S. PATENT DOCUMENTS

Figure 1:
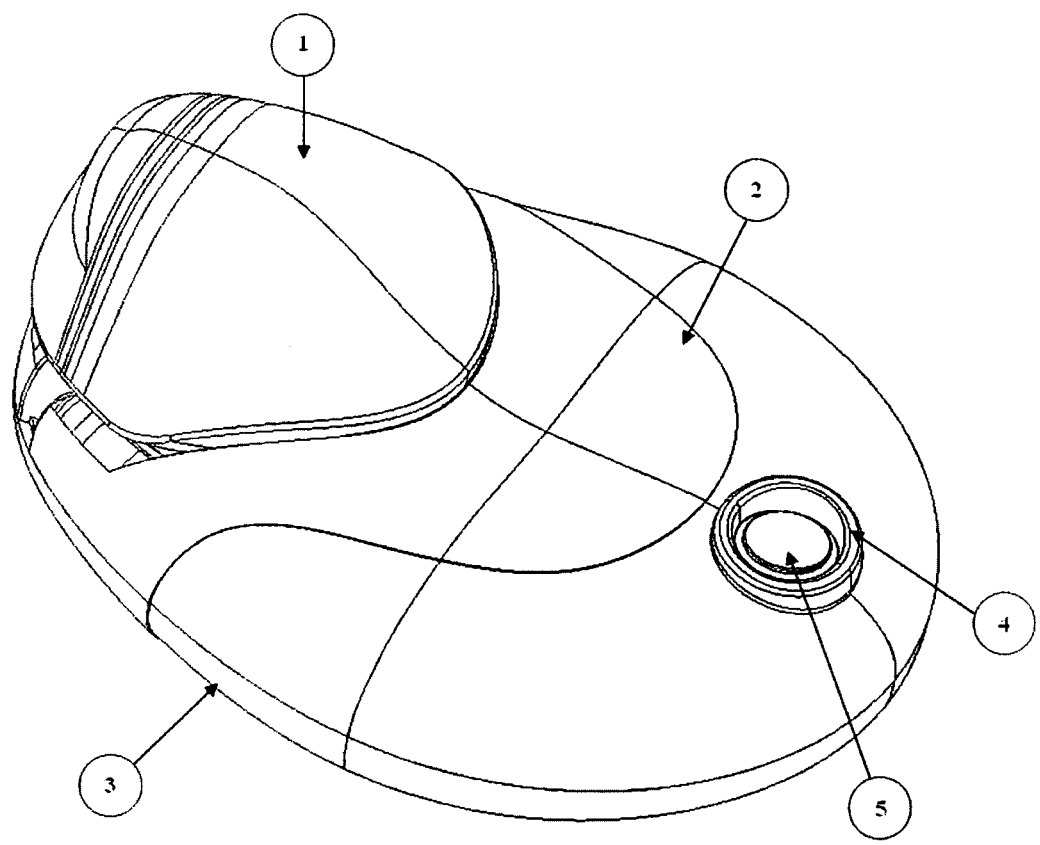

| | | |
|---|---|---|
| 2003/0172927 A1* | 9/2003 | Young et al. ............. 128/203.15 |
| 2005/0081851 A1 | 4/2005 | Young et al. |
| 2005/0081853 A1 | 4/2005 | Young et al. |
| 2005/0087188 A1 | 4/2005 | Young et al. |
| 2006/0005833 A1 | 1/2006 | Gieschen et al. |
| 2008/0099015 A1 | 5/2008 | Pocock et al. |
| 2008/0127973 A1 | 6/2008 | Pocock et al. |
| 2008/0163868 A1 | 7/2008 | Pocock et al. |

* cited by examiner

INHALATION DEVICE

FIELD OF THE INVENTION

The present invention relates to inhalation devices for the administration of medicament to patients for inhalation therapy.

BACKGROUND OF THE INVENTION

Inhalation-activatable dispensers for use with aerosol container assemblies are known, their general purpose being to afford proper co-ordination of the dispensing of a dose of medicament with the inhalation of the patient thereby allowing the maximum proportion of the dose of medicament to be drawn into the patient's bronchial passages. Recently breath actuated mechanism (BAM) or inhalation-activatable dry powder inhalers which combine the benefits of a dry powder inhaler with the convenience and ease of use of breath actuated mechanism are disclosed in some patents such as U.S. Pat. No. 5,408,994 and U.S. Pat. No. 6,880,555.

U.S. Pat. No. 5,408,994 relates to an inhalation device for administration of aerosolized medicament to the respiratory system of a patient comprising a housing defining a patient port in the form of a mouthpiece and an air inlet, the housing containing means for dispensing a dose of aerosolized medicament, an inhalation-activatable triggering mechanism for initiating the dispensing means, and reset means. The triggering mechanism comprises a vane mounted for pivotable movement between closed and open positions, the vane being positioned within the patient port such that inhalation through the patient port generates airflow from the air inlet to the patient port causing pivotable movement of the vane. The device further includes an activator component moveable between a restrained position and a dispensing position which movement causes dispensing of medicament from the dispensing means, the activator component being biased towards its dispensing position. This positioning of the vane in the mouthpiece has the disadvantage of the medicament getting deposited on the vane, leading to a probability of a sub-therapeutic dose as well as increasing the chances of microbial growth on the deposited particles on the vane.

U.S. Pat. No. 6,880,555 relates to an inhaler for medicament in powder form with an opening intended for inhalation. The powder medicament is arranged in the inhaler in a number of enclosures, each enclosure including a specific dose of medicament. A member is provided for enabling access to the dose of medicament. The member is arranged and designed such that it is able to be inserted inside the enclosure and establish at least one outlet passage, between the interior of the enclosure and the inhalation opening, through which outlet passage the medicament is delivered to the patient upon inhalation. It is disclosed that the elongate member serves as a source for air to enter into the interior of the inhaler and also the passage of the medicament from the enclosure into the respiratory tract of the patient. The inhaler is further provided with an activating means comprising a flap pivotally arranged adjacent an air intake and designed to be able of closing the air intake. A pressure spring is arranged for urging the flap to a closing position. Upon inhalation, air is forced through the passage of the elongated body from the interior of the inhaler, creating a pressure drop there and pressure difference between the interior and outside the inhaler. The pressure difference causes the flap to move around its pivot axis, thereby opening the air intake. The pivoting action of the flap causes the cantilever to pivot around its pivot axis, whereby the elongated body is pushed forward by its spring force, and its front end penetrating the blister cover of the blister placed in the wheel in a position in the longitudinal direction of the elongated body. This device has certain disadvantages. The primary disadvantage is the close association of the flap with the air inlet hole, which makes the device susceptible to triggering of the BAM and dispensing the dose even without inhalation if some external object were to exert a force on the flap through the air inlet hole. Additionally the device would be prone to clogging because of the air passageway through the narrow elongated body.

U.S. Pat. No. 6,948,494 relates to a medicament container to be used in a medicament inhalator, which is configured to improve entrainment of the medicament in the air and to improve deposition of the medicament in the lungs, comprising an upper layer and a bottom layer with medicament disposed there between. The upper layer is punctured to provide first and second openings to allow airflow to enter and exit through the upper layer of the medicament container. In a preferred embodiment, the medicament container has a projection which forms an elbow-shaped medicament containment/flow channel between the upper layer and the lower layer.

OBJECTS OF THE INVENTION

It is an object of the present invention to provide an inhalation-activatable device for administration of medicament in powder form to the respiratory system of a patient.

It is another object of the present invention to provide an inhalation-activatable device which does away with the problems associated with the prior art breath actuated mechanism devices by the proper positioning of the BAM flap such that it neither in the way of the air flow through the mouthpiece nor is it in close association with the air inlets.

It is yet another object of the present invention to provide an inhalation-activatable device having an air passageway which has the ability of tuning the aerosol performance of the device by changing or modifying the parameters of the components of the air passageway such that, each component of the air passageway, when varied would result in a different performance of the air passageway in a controlled and reproducible manner.

It is further object of the present invention to provide an inhalation-activatable device having a dose carrier with 60 dose units for administration of 60 doses of the medicament powder to the user.

It is still further object of the present invention to provide an inhalation-activatable device having a glow-in-the-dark feature to enable the user to locate the device in dark.

It is another object of the present invention to provide an inhalation-activatable device having a blind button to give an indication to the user that only the last 10 dose units of the dose carrier are remaining and that the rest of the dose units have been exhausted.

It is yet another object of the present invention to provide an inhalation-activatable device which gives feedback to the user about the proper use of the device in all the three steps of normal operation by the user.

It is still further object of the present invention to provide an inhalation-activatable device which operates independently of the user's inhalational efforts and would only operate at specified inhalation rates, for example, above about 40 liter/min and would give substantially constant doses even at higher inhalational rates.

It is yet another object of the present invention to provide an inhalation-activatable device which avoids wastage or double dosing associated with normal inhaling devices. Still other objects of the invention will be apparent to those of ordinary skilled in the art.

SUMMARY OF THE INVENTION

In one aspect of the invention there is provided an inhalation-activatable device for administration of medicament in powder form to the respiratory system of a patient.

In another aspect of the invention there is provided an inhalation-activatable device which does away with the problems associated with the prior art breath actuated mechanism devices by the proper positioning of the BAM flap such that it neither in the way of the air flow through the mouthpiece nor is it in close association with the air inlets.

In another aspect of the invention there is provided an inhalation-activatable device having an air passageway which has the ability of tuning the aerosol performance of the device by changing or modifying the parameters of the components of the air passageway such that, each component of the air passageway, when varied would result in a different performance of the air passageway in a controlled and reproducible manner.

In yet another aspect of the invention there is provided an inhalation-activatable device having a dose carrier with 60 dose units for administration of 60 doses of the medicament powder to the user.

In another aspect of the invention there is provided an inhalation-activatable device having a glow-in-the-dark feature to enable the user to locate the device in dark.

In a still further aspect of the invention there is provided an inhalation-activatable device having a blind button to give an indication to the user that only the last 10 dose units of the dose carrier are remaining and that the rest of the dose units have been exhausted.

It is yet another object of the present invention to provide an inhalation-activatable device which gives feedback to the user about the proper use of the device in all the three steps of normal operation by the user.

In a still further aspect of the invention there is provided an inhalation-activatable device which operates independently of the user's inhalational efforts and would only operate at specified inhalation rates, for example, above about 40 liter/min and would give substantially constant doses even at higher inhalational rates.

In another aspect of the invention there is provided an inhalation-activatable device which avoids wastage or double dosing associated with normal inhaling devices.

DETAILED DESCRIPTION OF THE INVENTION

The device of the present invention is illustrated by embodiments described here in below.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

FIG. 1: External view of the inhalation-activatable device with the cap closed FIG. 2: External view of the inhalation-activatable device with the cap open FIG. 3: External view of the inhalation-activatable device with the cap open FIG. 4: Top view of internal layout of the inhalation-activatable device, with the upper shell removed FIG. 5: Bottom view of internal layout of the inhalation-activatable device, with the lower shell removed FIG. 6: Exploded view of the inhalation-activatable device FIG. 7: Details of the BAM arrangement of the inhalation-activatable device FIG. 8: Details of the cam arrangement of the inhalation-activatable device FIG. 9: Schematic representation of the mechanism of the puncturing of the dose unit of the dose carrier of the inhalation-activatable device FIG. 10: Schematic illustration of air inlet array FIG. 11: Schematic illustration of converging cone section FIG. 12: Schematic representation of air passageway The figures only represent embodiments of the present invention. The embodiments are meant only for the purpose of illustration of the present invention. Different parts of the device of these embodiments are labeled in FIG. 1 to 9 and the labeling is described in the schedule of the reference numerals herein below.

SCHEDULE OF REFERENCE NUMERALS

| | |
|---|---|
| 1: | Cap or cover |
| 2: | Upper shell |
| 3: | Lower shell |
| 4: | Glow-in-the-dark feature |
| 5: | Lens |
| 6: | cyclone head of the air passageway |
| 7: | Yoke |
| 8: | Ducting |
| 9: | BAM flap |
| 10: | Bi-stable spring |
| 11: | Dose carrier |
| 12: | Blind button |
| 13: | Piercing beam |
| 14: | Cam |
| 15: | Indexer |
| 16: | Yoke spring |
| 17: | Primer spring or extension spring |
| 18: | Roll-off beam and peg |
| 19: | Hook of the cam |
| 20: | Cam track |
| 21: | Peg of cam |
| 22: | Mouthpiece |
| 23: | Air inlet holes |
| 24: | Cam foot |

The present invention relates to an inhalation-activatable device for administration of medicament in powder form to the respiratory system of a user comprising a housing defining air inlet(s) and a mouthpiece, and a cap for covering the mouthpiece, wherein the housing contains a dose carrier with medicament in powder form arranged in plurality of dose units and a breath activated mechanism comprising an energy storing means, a triggering means, and a reset means, in which the triggering means comprises a Breath Actuated Mechanism (BAM) flap mounted for movement between neutral and inner position, the BAM flap being positioned away from the mouthpiece and substantially away from the air inlet(s) so as not to close the air inlet(s) in its neutral or inner position, such that inhalation through the mouthpiece causes movement of the BAM flap to its inner position, and other components movable relative to the position of the BAM flap such that when the BAM flap is in the inner position, a dose unit of the plurality of dose units on the dose carrier is punctured to deliver the medicament in powder form through the flow path and the mouthpiece to the respiratory system of the user.

The inhalation-activatable device of the present invention uses a breath activated mechanism comprising an energy storing means, a triggering means, and a reset means for dispensing of the powder medicament to the user in just three steps of operation. The user has to open the cap of the inhalation device in order to store the energy required for triggering the BAM, in an energy storing device; inhale on the mouthpiece, in order activate the triggering means to puncture the dose unit of the medicament and carry the medicament to the mouthpiece and; close the cap in order to reset the BAM mechanism, so that the device is ready for use the next time the user opens the cap of the device.

The energy storing means of the inhalation-activatable device of the invention is a spring means used in conjunction with the cap used to close the mouthpiece of the device. The spring means may be any means known in the art. A compression/extension spring primed using linear motion obtained from the opening of the cap via a crank or piston is the preferred spring means. Alternatively a torsion spring, primed using linear motion obtained from the opening of the cap via a crank or piston can be used. Alternatively a pre-compressed compression spring may be used, wherein the opening of the cap will release the spring.

The BAM needs to be activated when the patient inhales through the devices creating a specified pressure drop. The triggering of the BAM must cause the piercing mechanism to fire. The triggering means of the inhalation-activatable device of the invention may preferably be a "roll-off mechanism", where a peg with a flap attached holds the stored energy from the spring means in place. When the user inhales, the flap is deflected and this causes the peg to rotate and "roll-off" the component it was restraining. The stored energy is then released and can be used in another mechanism. Alternatively a "Hook mechanism" can be used, which also uses a flap, which is deflected by the user's inhalation, but instead off causing a peg to rotate, the deflection of the flap pulls a hook out of the way of the component it was restraining. Alternatively a diaphragm which would flex, due to the pressure difference imposed across it when the user inhales, can be used. This flexing of the diaphragm would generate a deflection of the diaphragm that could be used to move a peg or hook. Alternatively the rotor and stator blade mechanism which comprises two sets of blades displaced relative to each other by the flow of air through the gaps between them, generated by the inhalation of the user, may be used. Alternatively, a component resembling a pair of bellows that expands and contracts during the presence of flow of air may be used. The displacement of this component is used to move a peg or hook.

The piercing mechanism must be actuated by the triggering of the BAM and can utilize the stored energy from the opening of the cap. The inhalation-activatable device of the invention uses a piercing beam which can puncture the dose unit of the dose carrier. It is preferred that the piercing beam has two puncturing piercing heads so as to make two punctures in the dose unit. It is further preferred that the piercing heads are solid and are not hollow in any part. The inhalation-activatable device of the invention may use the deflected beam piercing mechanism which uses a leaf spring like beam, which is primed by pulling it away from the dose unit, wherein when the BAM is fired, the restraining pin is released and the beam is free to deflect back past its neutral position and pierce the dose cavity. The beam would then return to its neutral position and would therefore retract itself from the cavity. Alternatively a linear cam driven using a piston may be used. The cam track would drive a component with the piercing heads on down into the cavity and out again. Alternatively a rotary cam which would drive a piercing component down into the cavity and allow it to return every time it is rotated through a specified angle, can be used. A preferred embodiment of the inhalation-activatable device of the invention uses a combination of the deflected beam and linear cam, wherein the leaf spring like beam would be driven by a linear cam. This would give the advantage of controlling the movement of the piercing beam and the puncturing beams in the dose unit and also the retraction of the beam after the piercing or puncturing of the dose unit.

The air passageway or airway is that part of the inhalational-activatable device, through which the air and the powder blend of the medicament in powder form and an optional excipient such as lactose, passes, upon a pressure drop generated by the inhalation of the user, into the mouth of the user. The air passageway is responsible for the aerosol performance of the inhalational device.

The principal function of the air passageway is to use the pressure drop generated by the patient and provide energy to the powder blend of the medicament in powder form and an optional excipient so that the medicament particles separate out from the excipient particles and the medicament particles are delivered to the lungs in a calibrated and controlled manner. The principal aim of the design of an air passageway is to maximize the airway performance which is characterized by its de-agglomeration potential, measured in terms of the Fine Particle Fraction as is known to the person skilled in the art, within the constraints such as possible pressure drops that can be generated by the patient, space and size envelope available to fit the air passageway into the inhalational device. The air passageway performance should be consistent across a range of possible pressure drops that can be generated by the varying range of flow rates generated by the user/users through the air passageway. The air passageway performance should be consistent such that there is minimum retention of the medicament powder or the excipient particles in the device. The air passageway performance should be consistent across a range of breath profiles i.e. pressure drops generated by the user as a function of time. Any suitable air passageway known in the prior art may be used in the inhalation-activatable device of the invention.

Figure 10:
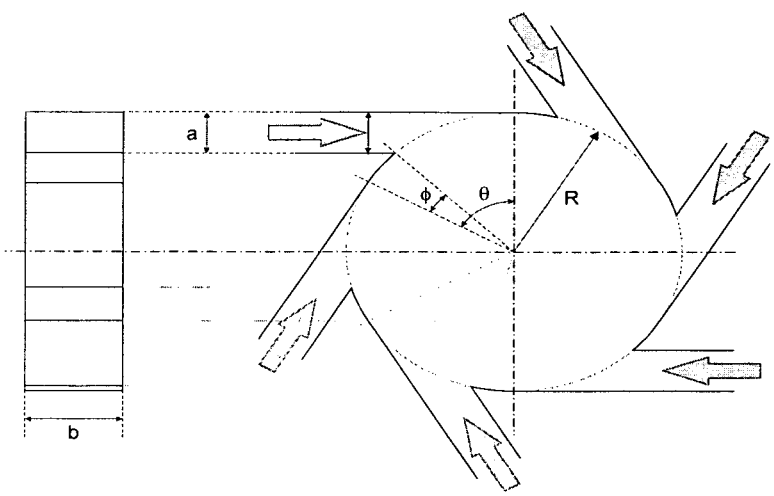
Figure 11:
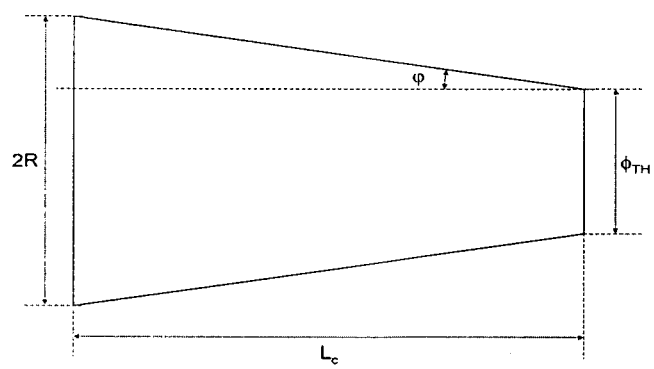
Figure 12:
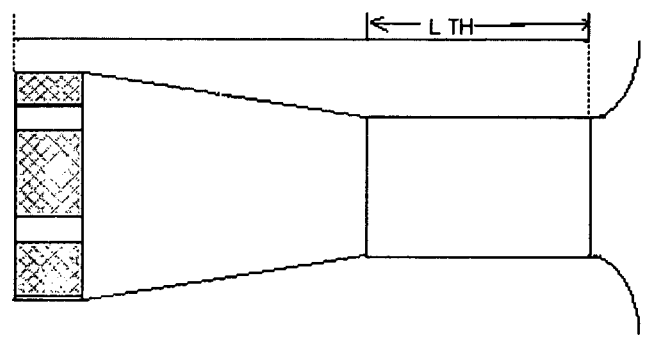

A preferred air passageway, which can be used in the inhalational-activatable device of the present invention, uses components, such that small changes in these components can be tuned to extract optimal performance in deagglomerating various formulations with different characteristics. The preferred air passageway is illustrated in FIG. 10, FIG. 11 and FIG. 12. With reference to FIG. 10, FIG. 11 and FIG. 12, the parameters shown in the figures are described herein below:

a=width of tangential air inlet (mm)
R=major radius of convergence cone (mm)
$\Phi$=effective dwell angle)(°)
b=length of tangential air inlet (mm)
$\phi$=convergence half-angle of cone (°)
$L_c$=length of the cone (mm)
$\Phi_{TH}$=throat diameter (mm)
$L_{TH}$=Throat Length This preferred air passageway has a cyclone head, a conical region, a throat region and vanes at the end of the air passageway. The cyclone head, which is elliptical in cross section, is responsible for setting up of a swirl of the medicament powder and air in the air passageway. The cyclone head has 2 or more tangential air inlets, wherein one of the air inlet is connected to the manifold through which the medicament powder from the ruptured dose unit is fed. The cyclone head further leads to a converging cone shape and then to the throat of the air passageway, all of which are elliptical in cross section. A net swirl of the medicament powder and air generated in the cyclone head is increased by reducing the elliptical cross sectional area in the conical region, thereby increasing the tangential velocity component of the swirl. The converging conical region acts to increase the swirl velocity of the medicament powder and air and the shear-strain in the swirling loaded air in order to enhance the particle-particle collisions and also separate out the heavier particles from the lighter ones. The throat is the smallest constant elliptical cross section along the axial direction downstream. A high swirl of the medicament powder and air is fed into this region and the constant small cross section of the throat contributes to sustaining the swirl for a longer length and time. This is the region where maximum de-agglomeration occurs in the airway. Further, downstream of the throat region are the vanes. The vanes help reduce the swirl of the exiting de-agglomerated cloud. The vanes are designed in such a way that they make the entire swirl rotate in the opposite direction, thereby reducing the net tangential velocity and the overall axial velocity. The principal function of the vanes is to deliver high swirling excipient particles and a low swirling medicament powder cloud that enters the patient's mouth.

The air passageway described above, has the ability of tuning the aerosol performance by changing or modifying the parameters of the components of the air passageway. Each component of the air passageway, when varied would result in a different performance of the air passageway in a controlled and reproducible manner. For example, the amount of swirl generated in the cyclone head can be controlled by varying the number of inlets, the amount of increase of the swirl can be controlled in a parametric way by varying the cone angle and the axial length of the conical section, the net peak swirl generated in the air passageway can be controlled by the effective elliptical cross-section of the throat and the axial length of the throat section, the net desired output swirl can be controlled by the pitch and length of the vanes. Two such air passageways (Airway A and Airway B) with modified parameters of its components are shown in Table 1. The pressure mapping data of the two airways (Airway A and Airway B) are shown in Table 2 and its aerosol performance in terms of fine particle fraction with respect to emitted dose for Long Acting Beta Agonists (LABA) and Inhaled Corticosteroid (ICS) in different pressure drop are shown in Table 3.

TABLE 1

Airway dimension of two sample airways

| Component Description | Symbols | Units | Airway A | Airway B |
|---|---|---|---|---|
| Number of Inlets | $n_i$ | No.s | 5.0 | 5.0 |
| Throat diameter | $\Phi_{TH}$ | mm | 8.7 | 9.41 |
| Inlet width | a | mm | 3.5 | 3.5 |
| Inlet height | b | Mm | 2.066 | 1.926 |
| Dwell angle | $\Phi$ | deg. | 11.5 | 11.7 |
| Convergence ½ angle | $\phi$ | deg | 28.6 | 28.6 |
| Throat length | $L_{TH}$ | mm | 13.26 | 13.98 |

TABLE 2

Pressure mapping of the two airways A and B

| Pressure drop (kPa) | Flow rate (Liter/min) | |
|---|---|---|
| | Airway A | Airway B |
| 1 | 26 | 26 |
| 2 | 40 | 43 |
| 3 | 50 | 53 |
| 4 | 59 | 64 |
| 5 | 68 | 73 |
| 6 | 76 | 83 |
| 7 | 83 | 90 |
| 8 | 90 | 97 |

TABLE 3

Pressure Drop ($D_p$) Vs Fine Particle Fraction (FPF) with respect to Emitted Dose (ED)

| | Blend X | | | |
|---|---|---|---|---|
| | Airway A | | Airway B | |
| Differential pressure (kPa) | LABA FPF ED | ICS FPF ED | LABA FPF ED | ICS FPF ED |
| 2 | 39.764 | 46.198 | 45.524 | 51.005 |
| 4 | 47.277 | 50.732 | 54.012 | 58.131 |
| 6 | 48.782 | 53.007 | 54.719 | 58.432 |

Figure 2:
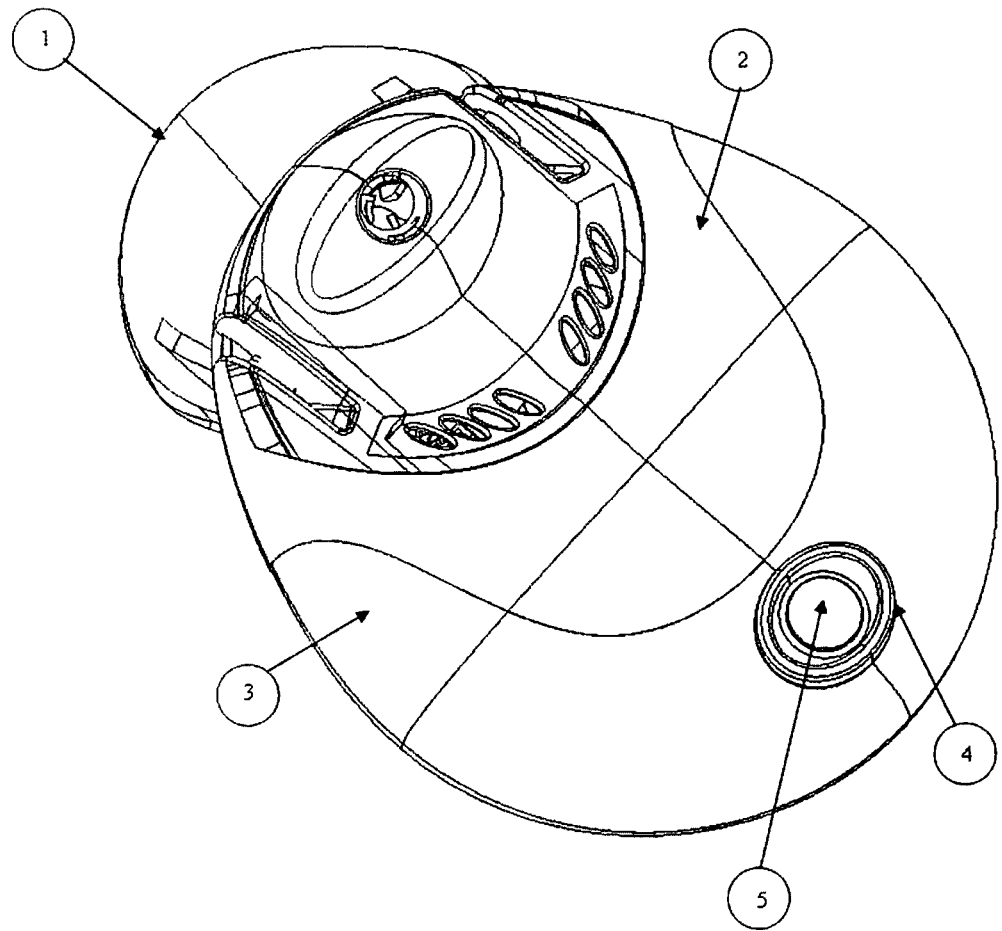
Figure 3:
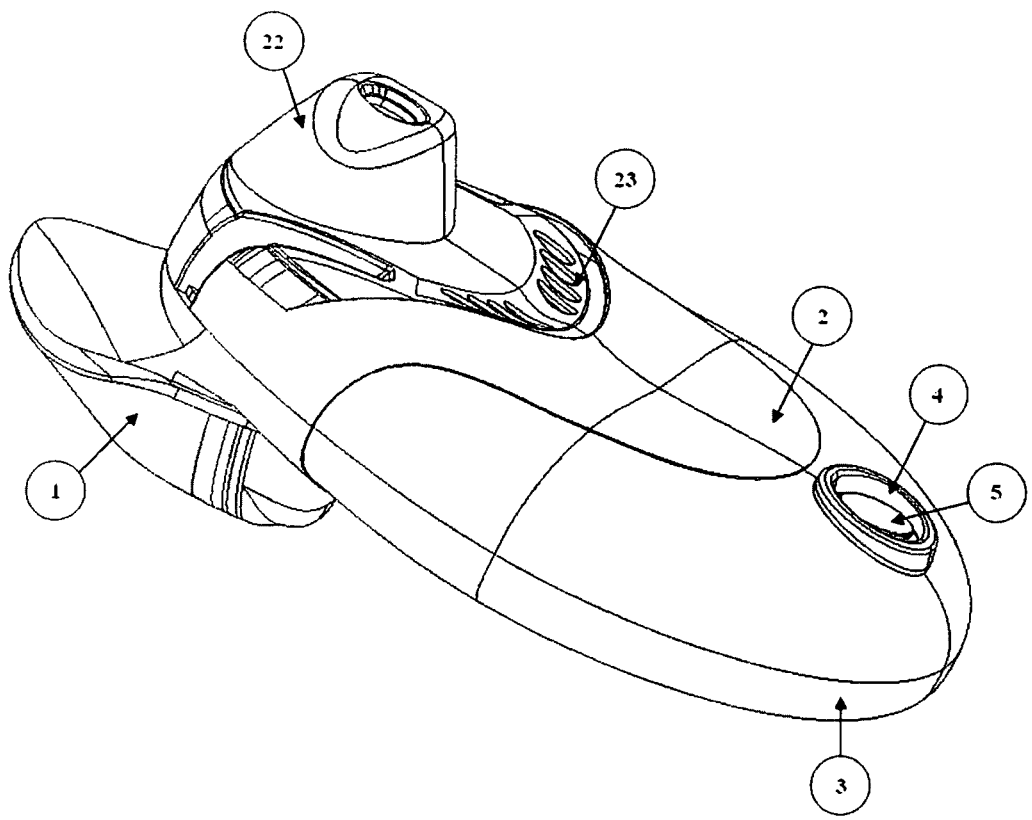
Figure 4:
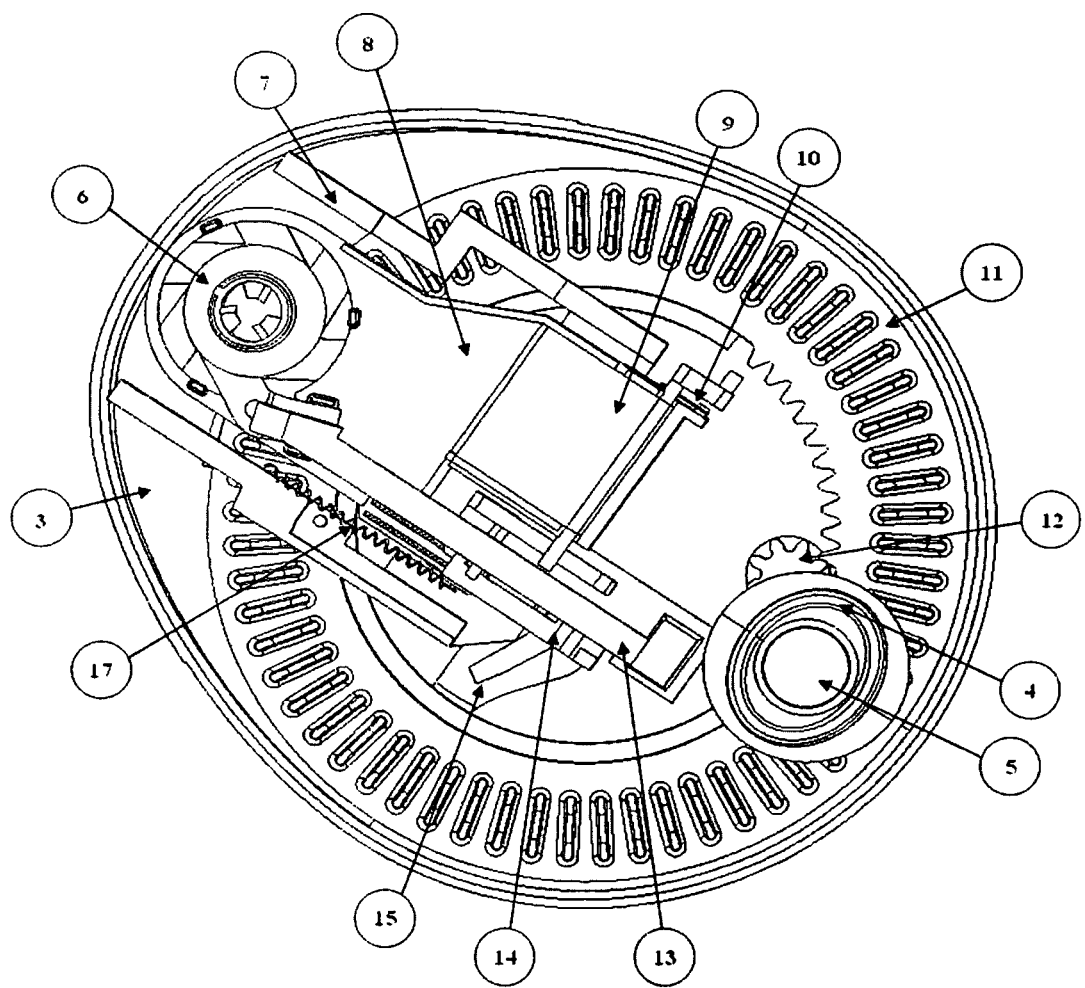
Figure 5:
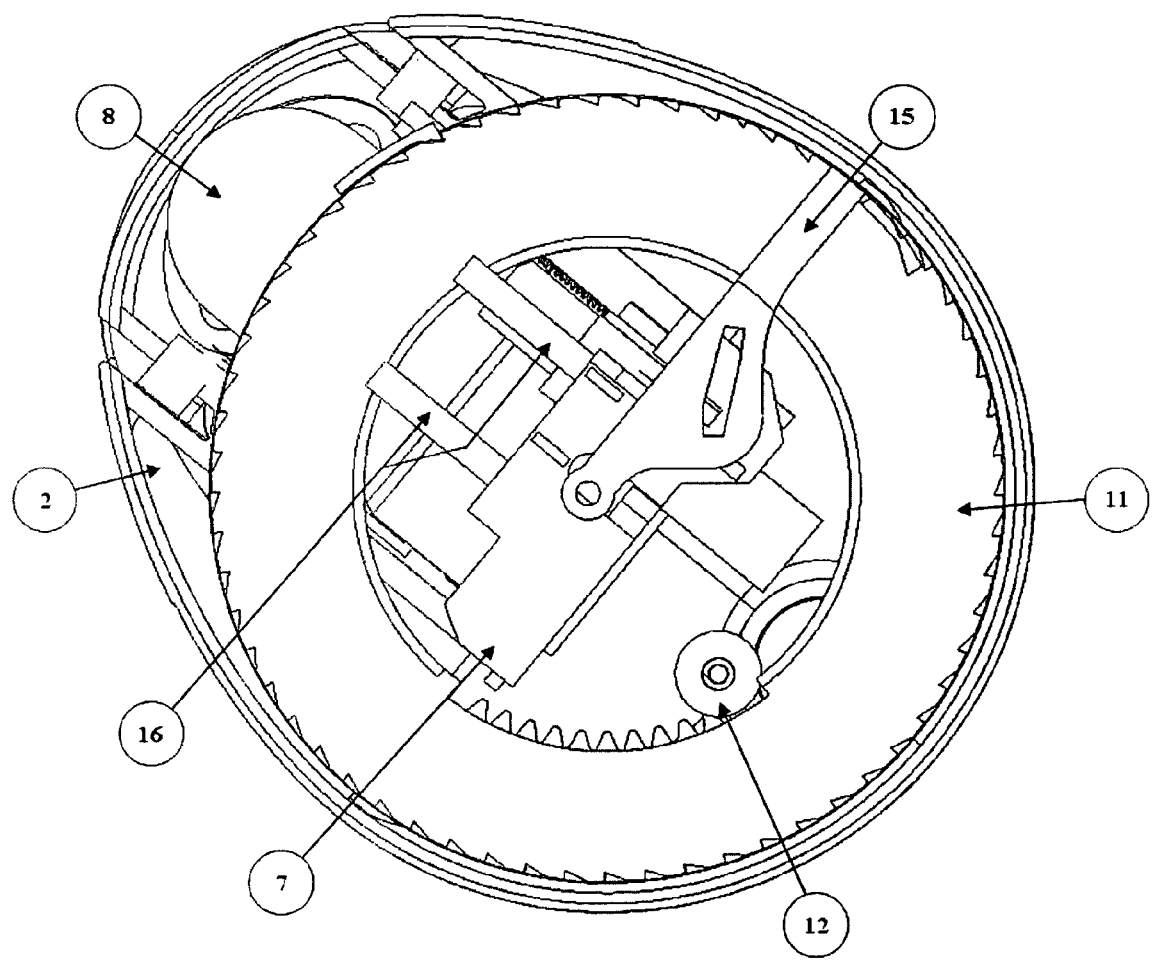
Figure 6:
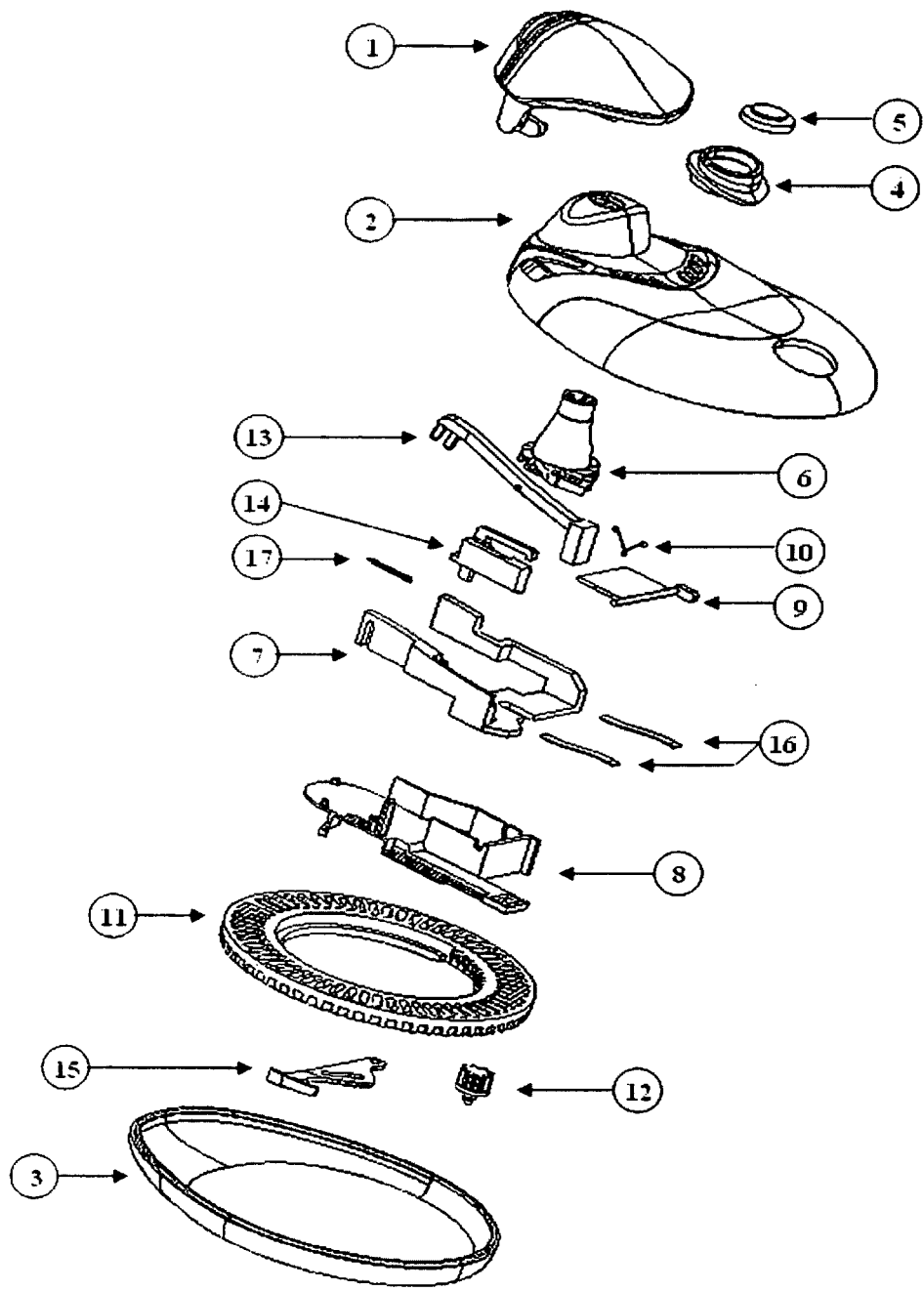

An embodiment of the inhalation-activatable device of the invention is shown in FIG. 1 to 9 and is described below. An exploded view of some of the components of the inhalation-activatable device of the invention is shown in FIG. 6. This embodiment relates to an inhalation-activatable device which has a housing made of an upper shell (2) and lower shell (3). The housing defines air inlet(s) (23) and a patient port in the form of a mouthpiece (22). The air inlets are present on the top of the device on the upper shell of the housing. There is a cap or cover (1) for covering the mouthpiece (22) when the device is not in use (FIGS. 1, 2 and 3). The cap is opened from front/top to back/bottom of the device around a pivot.

The dose carrier (11) with medicament in powder form arranged in plurality of dose units is a disk comprising a plurality of medicament containing cavities which is closed on one side and sealed with a lidding material such as foil layers or foil laminates or other such suitable materials on the other sides (FIGS. 4 and 5). The dose carrier is mounted on ribs on the lower shell (3) of the housing and has ratchets on the outside surface of its circumference to interface with an indexer. The dose carrier (11) has the dose numbers corresponding to each unit dose provided on it, for easy viewing by the user through a lens (5) mounted on the upper shell (2).

The cap (1) of the device is connected to a yoke (7) which runs on the ribs on the lower and upper shells (FIG. 5). The yoke (7) is driven by the opening and closing of the cap (1). It also returns the cam (14) to the starting position on closing of the cap (1). The yoke (7) has a yoke spring (16) mounted on it to provide a good seal with the dose carrier (11) when the cap (1) is opened and the yoke (7) is pulled towards the cap (1) (FIG. 5). On the yoke (7) is also mounted a primer spring or extension spring (17) which is a tension mounted spring attached to the cam (14) (FIG. 4). The extension spring provides the drive energy when the cap (1) is opened, which is released by the BAM triggering mechanism on inspiration by the use.

Figure 7:
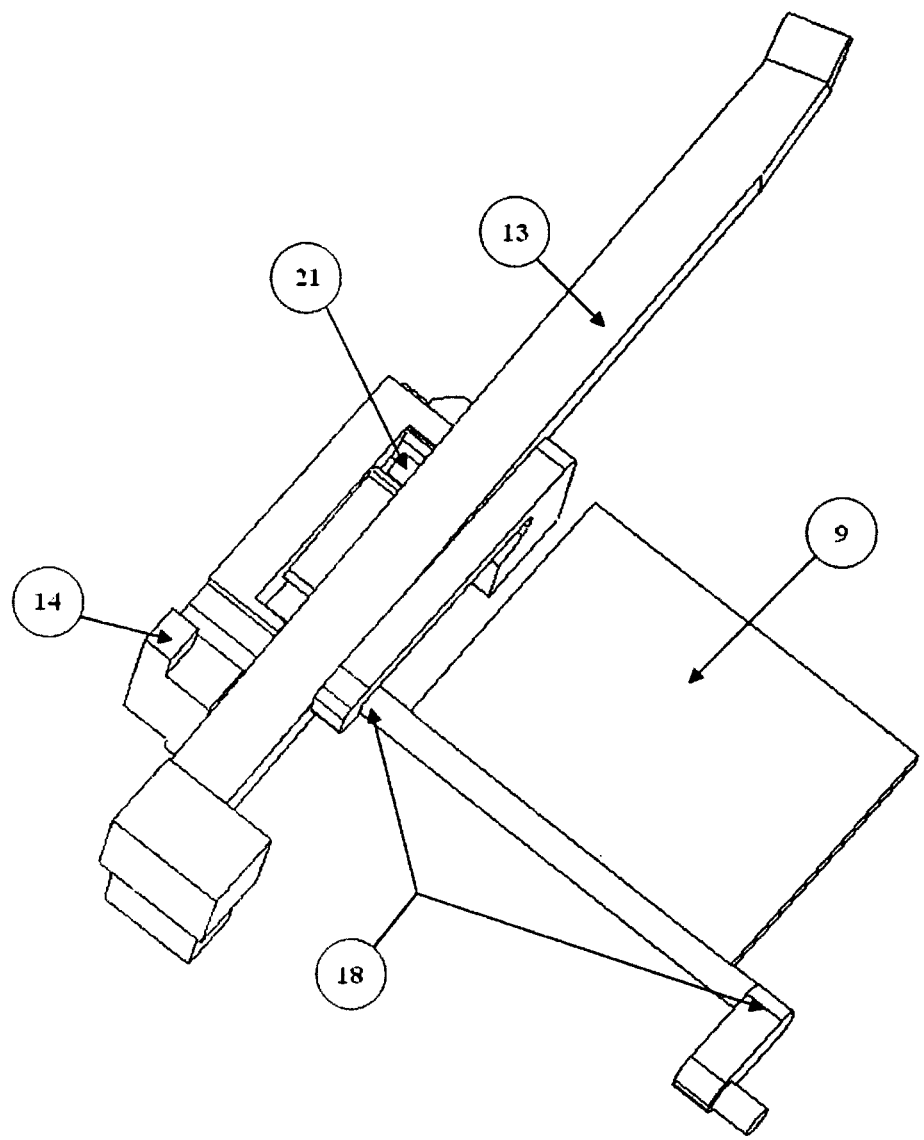
Figure 8:
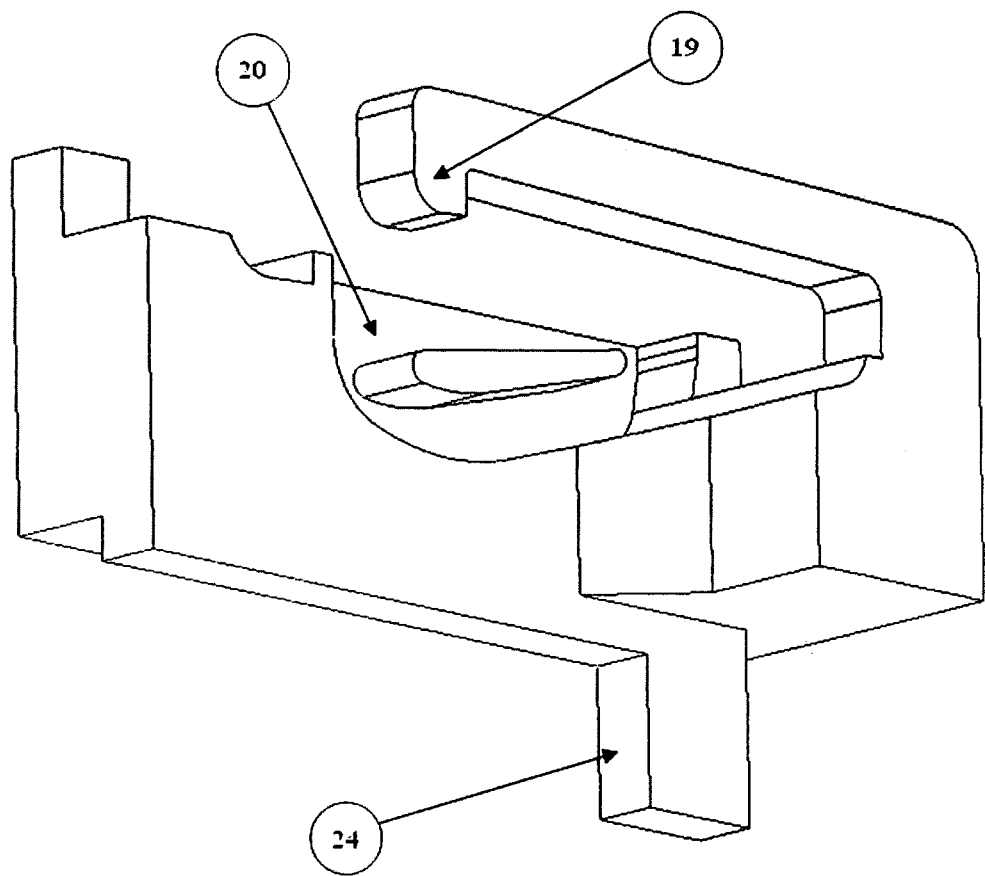

There is a BAM flap (9) mounted on the lower shell (3) of the device. The BAM flap (9) is held in position by a bi-stable spring (10) (FIG. 4). The BAM flap (9) has a big flap area to utilize the breath pressure differential caused by inhalation by the user (FIG. 7). Due to the breath pressure differential caused by inhalation by the user, the BAM flap (9) falls from its original position. The BAM flap (9) at its axis has a roll-off beam and peg. (18) (FIG. 7). The roll-off beam and peg (18) of the BAM flap holds in place the hook of the cam (19) (FIG. 8). The hook of the cam (19) when released from the roll-off beam and a peg (18) of the BAM flap will set into motion the triggering of the BAM mechanism. The cam (14) in addition to the cam hook (19) also has the cam foot (24) (FIG. 8) which collects the indexer (15) to move it to the next ratchet of the dose carrier (11) (FIG. 5). The cam (14) slides between ribs on upper and lower shell and has a mounting point for the primer spring (17) which drives the cam (14) when the breath actuated mechanism of the device is activated by inhalation (FIG. 4). The cam (14) has a cam track (20) and a cam peg (21) moving on the cam track (20) (FIGS. 7 and 8). The cam peg (21) is attached to the piercing beam (13) at one end (FIG. 7) and has its other end, two solid piercing heads for puncturing the foil on one side of the dose unit of the dose carrier (11). When the cam (14) moves linearly forward, the cam peg (21) moves in a vertical direction because of the cam track (20) profile and the piercing beam (13) moves down and punctures the foil of the dose unit of the dose carrier (11) at two places on one side of the dose unit and retracts back to the resting position.

The inhalation-activatable device of the invention has air inlets holes (23) on upper shell (2) through which air will enter into the device on inhalation by the user (FIGS. 2 and 3) by passing through a ducting (8) and into the passage/opening created by the fallen BAM flap in the inner position (9) (FIG. 4). The device also has air passageway comprising a cyclone head, a conical region, a throat region and vanes at the end of the air passageway. The air passageway is assembled into mouthpiece tube on upper shell (2). This air passageway has a cyclone head (6), which is elliptical in cross-section and has six inlets through which the entrained medicament powder and air will enter and mix to form a swirl or cyclone for deagglomeration of the medicament particles (FIG. 7). The cyclone head further leads to a conical shape and further to a throat region. There are three spiral vanes at the end of the elliptical air passageway (6) (FIG. 7) to break the swirling motion of the powder stream exiting out of the air pathway and also to decrease the velocity of the powder stream. This is so as to avoid the powder stream impinging at the back of the throat.

There is a blind button (12) provided in the lower shell (3) to give an indication to the user that only the last 10 dose units of the dose carrier are remaining and that the rest of the dose units have been exhausted. The blind button (12) has ratchets to engage in the gear teeth provided on the last ten doses of the carrier dose (11) (FIG. 4). As the dose carrier (11) is advanced beyond the last ten dose units, the blind button (12) advances along the gear teeth and protrudes out on the lower surface of the device. As more doses are consumed, the button protrudes more and when the last dose of the dose carrier is consumed, the blind button (12) will lock the further movement of the dose carrier (11). When the button protrudes out, it also causes the device to rock when placed on the flat surface giving one more indication to the user that it needs replacement There is a lens (5) mounted in the glow-in-the-dark feature (4) on the top of the upper shell (2) (FIGS. 1, 2, 3, 4 and 6) to aid the user in viewing the dose number of dose unit being consumed which is provided on the dose carrier (11). The glow-in-the-dark feature (4) glows in the dark to enable the user to locate the device in dark.

The working of the inhalation-activatable device of the invention is given below:

When Cap is Opened:

Initially the primer spring or the extension spring (17) mounted between the yoke (7) and the cam (14), is in a relaxed position. When the cap (1) is flipped back or opened, the yoke (7) is moved towards the cap (1). This causes the primer spring (17) to be stretched or extended. When the yoke (7) is pulled towards the cap (1), the yoke spring (16) moves under the dose carrier (11).

When the User Inhales Through the Mouthpiece:

The inhalational device of this embodiment is used by the user in a vertical orientation The user will hold the lower shell/back side of the inhalation device in his palm and raise his palm to his mouth to put his mouth on the mouthpiece such that the inhalational device is at a position vertical to the horizontal axis, such that the opened cap is pointing upwards and the lens with the dose number is at the bottom When the user inhales/sucks at the mouthpiece (22) of the inhalation-activatable device of the invention, situated above the air passageway (6), the inhalation-activatable triggering mechanism comes into play. A negative pressure or pressure drop is created in the device below the Breath Actuated Mechanism (BAM) flap (9) which is attached to a bi-stable spring (10). This causes the BAM flap (9) to fall/move inward. When the BAM flap (9) falls, the roll-off beam and peg (18) rolls, releasing the hook of the cam (19). As the cam (14) is held by the primer spring/extension spring (17) which has been stretched by the flipping of the cap (1), when the hook of the cam (19) is released, the cam (14) will move in the direction of the cap (1). When the cam (14) moves linearly forward, the cam peg (21) with the piercing beam (13) moves in a vertical direction because of the cam track (20) profile and the piercing beam (13) moves down and punctures the lidding material/foil of the dose unit of the dose carrier (11) at two places on one side of the dose unit and retracts back to the resting position.

Figure 9:
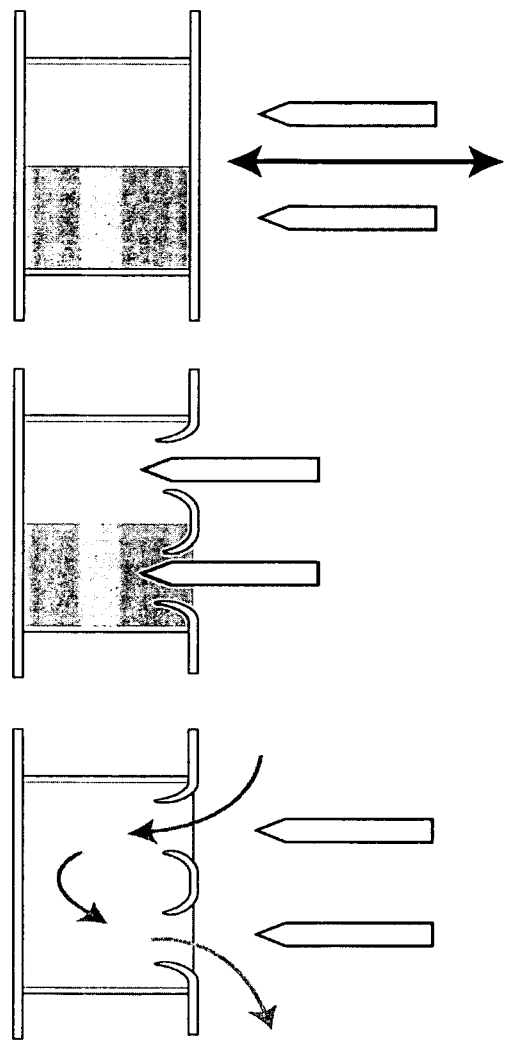

As the inhalation device is kept in a vertical orientation to the horizontal axis, during use, by the user, the dose carrier (11) too will in a vertical orientation to the horizontal axis, during use. As the dose carrier is in a vertical position, the dose unit of the dose carrier too will be in a vertical position. In vertical position, the powdered medicament will be settled at the bottom of the dose unit of the dose carrier (11) (FIG. 9). When the inhalation-activatable triggering mechanism is activated by inhalation, the piercing beam (13) will move down, as described earlier, and puncture the lidding material or the foil of the dose unit of the dose carrier (11) at two places on one side of the dose unit and retract back out of the punctures (FIG. 9).

When the patient has sucked on the mouthpiece, the air is drawn in through the air inlet holes (23) on the top of the upper shell (2) of the inhaler into the device, by passing through the ducting (8) and into the passage/opening created by the fallen BAM flap (9). Air enters the puncture on the top of the side of the punctured dose unit of the dose carrier, entrains the medication powder and exits through the second punctured hole at the bottom of the same dose unit into the manifold and into the inlet of the cyclone head (6). Simultaneously air also enters the cyclone head (6) from the other five inlets of the air pathway and mixes to form a swirl or cyclone for deagglomeration of the drug particles. The aerosolized powder medicament is then led through a conical area into a throat area and onto the spiral vanes at the end of the passageway. The three spiral vanes at the end of the elliptical air passageway (6) act to break the swirling motion of the powder stream exiting out of the air passageway and also to decrease the velocity of the powder stream.

During inhalation, when the cam (14) moves towards the direction of the cap (1), the cam foot (24) collects the indexer (15) and bumps it to the next ratchet of the dose carrier (11). When the Cap is Closed:

When the cap (1) is closed, the reset mechanism springs into play. The yoke (7) moves away from the cap (1) whereby the yoke spring (16) is removed from beneath the dose carrier (11). The movement of the yoke (7), causes the extension spring (17) to regain its original relaxed position and pushes the cam (14) back to its original position causing engagement of the hook of the cam (19) with the roll-off beam and peg (18). This also pushes the roll-off beam and peg (18) to move the BAM flap (9), which is held in place by the bi-stable spring, to its original neutral position again.

As the cam (14) moves away, the cam foot (24) collects the indexer (15) and advances the dose carrier (11) to the next dose unit.

An embodiment of the inhalation-activatable device of the invention was described above with regards to FIG. 1-9. But it is apparent that additional embodiments and modifications of the above embodiment without departing from the spirit of or exceeding the scope of the claimed invention can be done and are covered within the scope of this invention.

In an embodiment, the housing of the inhalation-activatable device of the invention may be in the form of a single piece instead of two shells. Optionally it can be in more than two pieces or shells.

In an embodiment, the cap of the inhalation-activatable device of the invention may be opened sliding sideways around the device instead of the front/top to back/bottom opening around a pivot as shown in the preferred embodiment described above.

In an embodiment, the dose carrier of the inhalation-activatable device of the invention may be open on both sides and may be covered by lidding material such as foil layers or foil laminates or other such suitable materials on the both the sides.

The dose carrier used in the inhalation-activatable device of the invention has been designed to have multiple cavities. It is also necessary that the material of construction be suitable since it needs to function as a Primary packaging component along with the lidding material. The dose carrier may be made from a plastic moulded/thermoformed component made from a polymer which can provide the needed water vapour transmission rate and oxygen permeability specifications. The polymers used for this purpose may be cycloolefin copolymer (COC) or polypropylene (PP) or polyvinyl chloride (PVC) or polyethylene (PE) or polycarbonate (PC) or polyvinylidene chloride (PVDC) or liquid crystal polymer (LCP) or Xenoy®, which is a blend of semi-crystalline polyester (typically polybutylene terephthalate (PBT) or polyethylene terephthalate (PET) and polycarbonate (PC)) or Nylons or the like or combination thereof to create one or more layers during the moulding process. However many of these polymers while having a good barrier properties for oxygen do not have a good barrier against moisture and vice versa. To overcome this limitation, the cavities of the dose carrier can be formed/moulded from a high moisture barrier material like COC in the first layer and overmoulded with a good gas barrier material as the second layer.

The dose carrier of the inhalation-activatable device of the invention has plurality of dose units. Any suitable number of the dose units can be present on the dose carrier depending on the size of the dose carrier. The dose carrier may have dose units ranging from about 10 units to about 120 units. In a preferred embodiment the dose carrier has 60 dose units arranged side-by side along its circumference.

In an embodiment, the air passageway of the inhalation-activatable device of the invention may be of any shape or size known in the art. The cyclone head of the air passageway may be elliptical, circular, or of any other suitable shape in its cross-section. The cyclone head may be rotationally symmetrical in an arcuate shape along the longitudinal central axis of the air passageway. In a preferred embodiment, the cyclone head as shown in FIG. 4 has an elliptical cross section and is not rotationally symmetrical along the longitudinal central axis of the air passageway. The cyclone head may have a single inlet or a plurality of inlets. In a preferred embodiment, there may be six inlets to the cyclone head, wherein one of the inlet is for the entry of the medicament powder. There may additionally, be a plurality of vanes present in the air passageway. In an embodiment there may be no vanes present in the air passageway. A preferred embodiment as shown in the FIG. 3 has three vanes at the end of the air passageway.

In an embodiment of the inhalation-activatable device of the invention, the dose unit of the dose carrier is punctured by the piercing heads of the piercing beam in such a way that both the punctured holes are of the same size as one another. In another embodiment of the present invention, the dose unit of the dose carrier is punctured by the piercing heads of the piercing beam in such a way that one of the punctured holes is bigger than the second punctured hole. It is preferred that the punctured hole of the dose unit which allows the ingress of air into the punctured dose unit is smaller than the punctured hole of the dose unit through which the air with entrained medicament exits. This is because the smaller punctured hole of the dose unit causes the air flow into the punctured dose unit at a high velocity causing better entrainment of the medicament in the air flow which exits through the second punctured hole of the dose unit into the air passageway and into the user's mouth. In a preferred embodiment, the dose carrier is in a vertical configuration to the horizontal axis, which causes the dose unit of the dose carrier to be in a vertical position. In this embodiment, the dose unit of the dose carrier is punctured by the piercing heads of the piercing beam in such a way that the puncture hole on the top of the dose unit is smaller than the puncture hole at the bottom of the dose unit.

In an embodiment of the present invention, the inhalation-activatable device of the invention gives feedback to the user about the proper use of the device in all the three steps of normal operation by the user. When the user opens the cap, there is tactile feel and an audible click sound indicating the proper execution of the first operation. When the user inhales, there is an audible sound of the striking of the piercing beam against the dose carrier indicating the proper execution of the second operation. When the cap is closed, the tactile feel and an audible sound is provided by the movement of the dose carrier indicating the proper execution of the final step.

In an embodiment of the present invention, the inhalation-activatable device of the invention operates independently of the user's inhalational efforts. The device would only operate at inhalation rates above about 40 liter/min and would give substantially constant doses even at higher inhalational rates.

In an embodiment of the present invention, the inhalation-activatable device of the invention avoids wastage or double dosing associated with normal inhaling devices. In this embodiment, the device would only operate at inhalation rates above about 40 liter/min and hence sub-inhalational efforts would not trigger the BAM mechanism and dispense any dose of the medicament. This would help to reduce accidental double dosing by the patient. Also if the cap of the device is opened, but the user does not inhale, the BAM is not triggered, thus avoiding wastage of the medicament.

In an embodiment of the present invention, the inhalation-activatable device of the invention may have its surface or any part of the surface made of an anti-slip material so as to enable the user to enable the user to grip the device properly.

In all the above embodiments, any one or all the components of the inhalation-activatable device of the invention can be made photo luminescent to enable the patient to access the device even in darkness. The various components of the device can be made transparent or translucent in order to make easy the visualization of the used or unused dose units of the dose carrier. Also a "soft feel" material can be incorporated in any of the components of the inhalation-activatable device of the invention, preferably the sides of the device where the patient grips the dry powder inhaler in order to administer a dose. The "soft feel" material used may be a TPE (Thermoplastic elastomer) with a shore hardness of about 30 to about 50.

In the embodiments described above, reference is made to a mouthpiece. However, if the inhalation-activatable device of the invention was to be used for purposes other than oral inhalation some other outlet would be employed, e.g. a nosepiece. In a preferred embodiment the inhalation-activatable device of the invention has a mouthpiece for the user to put in mouth and inhale. In another embodiment, the inhalation-activatable device of the invention has a nosepiece instead of a mouthpiece.

The inhalation-activatable device of the invention is suitable for dispensing medicament, particularly for the treatment of respiratory disorders such as asthma and chronic obstructive pulmonary disease (COPD) and for local action in the lungs. This inhalation activatable device can be used for delivery of medicament to the lungs for systemic absorption. The inhalational device of the invention is used to administer medicament in the form of powder. The powder medicament may be used as such or as a formulation with other excipients such as diluents for example, lactose. Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (eg s the sodium salt), ketotifen or nedocromil (eg as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (eg as the dipropionate ester), fluticasone (eg as the propionate ester), flunisolide, budesonide, rofleponide, mometasone eg as the furoate ester), ciclesonide, triamcinolone (eg as the acetonide) or 6α,9α-difluoro-11β-hydroxy-16α-methyl-3-oxo-17α-propionyloxy-androsta-1,4-diene-17β-carbothioic acid S-(2-oxo-tetrahydro-furan-3-yl) ester; antitussives, e.g., noscapine; bronchodilators, e.g., albuterol (eg as free base or sulphate), salmeterol (eg as xinafoate), ephedrine, adrenaline, fenoterol (eg as hydrobromide), formoterol (eg as fumarate), isoprenaline, metaproterenol, phenylephrine, phenylpropanolamine, pirbuterol (eg as acetate), reproterol (eg as hydrochloride), rimiterol, terbutaline (eg as sulphate), isoetharine, tulobuterol or 4-hydroxy-7-[2-[[2-[[3-(2-phenylethoxy) propyl]sulfonyl]ethyl]aminolethyl-2(3H)-benzothiazolone; adenosine 2a agonists, eg 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate); α$_4$integrin inhibitors eg (2S)-3-[4({[4-(aminocarbonyl)-1-piperidinyl]carbonyl}oxy)phenyl]-2-[((2S)-4-methyl-2-{[2-(2-methylphenoxy)acetyl]amino}penta-noyl)amino]propanoic acid (e.g. as free acid or potassium salt), diuretics, e.g., amiloride; anticholinergics, e.g., ipratropium (eg as bromide), tiotropium, atropine or oxitropium; hormones, e.g. cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament. Some of the preferred medicaments are selected from albuterol, salmeterol, fluticasone propionate and beclomethasone dipropionate and salts or solvates thereof, e.g., the sulphate of albuterol and the xinafoate of salmeterol. Medicaments can also be delivered in combinations. Some of the preferred formulations containing combinations of active ingredients contain salbutamol (e.g., as the free base or the sulphate salt) or salmeterol (e.g., as the xinafoate salt) or formoterol (eg as the fumarate salt) in combination with an antiinflammatory steroid such as a beclomethasone ester (e.g., the dipropionate) or a fluticasone ester (e.g., the propionate) or budesonide. A preferred combination is a combination of fluticasone propionate and salmeterol, or a salt thereof (particularly the xinafoate salt) or a combination of budesonide and formoterol (e.g. as the fumarate salt).

In one embodiment, the inhalation-activatable device of the present invention is capable of delivering from 1 mg to 50 mg of medication in a single dose by making suitable changes in the dose carrier and flow paths. The particle size of the carrier particles can range from about 20 μm to about 500 μm, preferably between 50 μm to 250 μm. The particle size of the active agent can vary from about 100 nm to 10 μm, preferably between 1 μm to 5 μm. The emitted dose from the device will be not less than 70%, preferably greater than 90% of the total dose.

Although the invention has been described in terms of particular embodiments and applications, one of ordinary skill in the art, in light of this teaching, can generate additional embodiments and modifications without departing from the spirit of or exceeding the scope of the claimed invention. It should be emphasized that the above-described embodiments of the present invention, particularly any "preferred" embodiments, are merely possible examples of the invention of implementations, merely set forth for a clear understanding of the principles of the invention. Accordingly, it is to be understood that the drawings and descriptions herein are proffered by way of example to facilitate comprehension of the invention and should not be construed to limit the scope thereof.

We claim:

1. An inhalation-activatable device for administration of medicament in powder form to the respiratory system of a user comprising a housing defining air inlet(s) and a mouthpiece, and a cap for covering the mouthpiece, wherein the housing contains a dose carrier with medicament in powder form arranged in plurality of dose units and a breath activated mechanism comprising an energy storing means, a triggering means, a piercing means and a reset means, in which the triggering means comprises a Breath Actuated Mechanism (BAM) flap mounted for movement between neutral or inward position, the BAM flap being positioned away from the mouthpiece and substantially away from the air inlet(s) so as not to close the air inlet(s) in its neutral or inward position, such that inhalation through the mouthpiece causes movement of the BAM flap to its inward position, and other components movable relative to the position of the BAM flap such that when the BAM flap is in the inward position, a dose unit of the plurality of dose units on the dose carrier is punctured by a piercing means to deliver the medicament in powder form through the mouthpiece to the respiratory system of the user, wherein the inhalation-activatable device further comprises an air passageway, wherein the air passageway comprises a cyclone head, a conical region, a throat region and vanes at the end of the air passageway.

2. An inhalation-activatable device as in claim 1, wherein the energy storing means is a spring means.

3. An inhalation-activatable device as in claim 2, wherein the spring means is a primer spring/extension spring.

4. An inhalation-activatable device as in claim 1, wherein the triggering means comprises the BAM flap and other components movable relative to the position of the BAM flap.

5. An inhalation-activatable device as in claim 4, wherein the BAM flap is held in its neutral or inward position by a bi-stable spring.

6. An inhalation-activatable device as in claim 4, wherein the other components movable relative to the position of the BAM flap comprise a roll-off beam and peg of the BAM flap and a hook of a cam.

7. An inhalation-activatable device as in claim 6, wherein the hook of the cam is held in place by the roll-off beam and peg of the BAM flap when the BAM flap is in neutral position.

8. An inhalation-activatable device as in claim 1, wherein the piercing means comprise a piercing beam having a pair of piercing heads for puncturing a lidding material of the dose unit of the dose carrier.

9. An inhalation-activatable device as in claim 8, wherein the piercing beam is attached to a peg moving on a cam track of the cam.

10. An inhalation-activatable device as in claim 8, wherein the piercing heads are solid.

11. An inhalation-activatable device as in claim 1, wherein the reset means of the breath activated mechanism comprises a yoke attached to the cap.

12. An inhalation-activatable device as in claim 11, wherein the reset means for the breath activated mechanism further comprises an extension spring mounted between the yoke and a cam.

13. An inhalation-activatable device as in claim 1, wherein the inhalation device is kept in a vertical orientation to the horizontal axis, during use, by the user.

14. An inhalation-activatable device as in claim 13, wherein the dose carrier is in a vertical orientation to the horizontal axis, during use, by the user.

15. An inhalation-activatable device as in claim 14, wherein the dose unit of the dose carrier is in a vertical orientation to the horizontal axis, during use, by the user.

16. An inhalation-activatable device as in claim 15, wherein the dose unit of the dose carrier is punctured by the piercing means having a pair of piercing heads.

17. An inhalation-activatable device as in claim 1, further comprising an indexer pivoted on the lower shell of the housing.

18. An inhalation-activatable device as in claim 1, further comprising a blind button mounted on the lower shell of the housing.

19. An inhalation-activatable device as in claim 1, further comprising a glow-in-the-dark feature mounted on the upper shell of the housing.

20. An inhalation-activatable device as in claim 1, wherein the cyclone head, the conical region and the throat region are elliptical in cross section.

* * * * *